(12) United States Patent
Salo

(10) Patent No.: US 7,631,569 B2
(45) Date of Patent: Dec. 15, 2009

(54) ARRANGEMENT FOR MOVING MEASURING HEAD OF MEASURING DEVICE INTO AND OUT OF PROCESS SPACE

(75) Inventor: Harri Salo, Vantaa (FI)

(73) Assignee: Janesko Oy, Vantaa (FI)

( * ) Notice: Subject to any disclaimer, the term of this patent is extended or adjusted under 35 U.S.C. 154(b) by 545 days.

(21) Appl. No.: 11/450,386

(22) Filed: Jun. 12, 2006

(65) Prior Publication Data

US 2007/0051194 A1 Mar. 8, 2007

(30) Foreign Application Priority Data

Jun. 17, 2005 (FI) .................................. 20055320

(51) Int. Cl.
*G01D 11/00* (2006.01)
(52) U.S. Cl. ..................................................... 73/866.5
(58) Field of Classification Search ..... 73/53.03–53.04, 73/866.5; 162/49, 198, 263
See application file for complete search history.

(56) References Cited

U.S. PATENT DOCUMENTS

| 4,275,592 | A  |   | 6/1981 | Atwood et al. |
| 5,009,113 | A  |   | 4/1991 | Kamrat |
| 6,338,359 | B1 |   | 1/2002 | Welker |
| 6,357,470 | B1 |   | 3/2002 | Evans et al. |
| 7,267,793 | B2 | * | 9/2007 | Poor et al. ................... 266/250 |
| 7,472,615 | B2 | * | 1/2009 | Mayeaux .................... 73/866.5 |

FOREIGN PATENT DOCUMENTS

| FI | 84400 | 8/1991 |
| JP | 5-99703 | 4/1993 |

OTHER PUBLICATIONS

Office Action of the corresponding Finnish priority application dated Dec. 12, 2005, (in Finnish.

* cited by examiner

*Primary Examiner*—Thomas P Noland
(74) *Attorney, Agent, or Firm*—Buchanan Ingersoll & Rooney PC

(57) ABSTRACT

An arrangement for moving a measuring head of a measuring device into and out of a process space. The arrangement includes a valve member that is attached to a wall of the process space. A measuring device is attached to the valve member and includes a body part provided with an elongated portion which in turn has a measuring head at one end. The measurement device also includes a placement device arranged to seize the measuring device and to move it through the valve member into a first position in which the measuring head extends into the process space and, correspondingly, into a second position in which the measuring head is not in contact with the process space. The placement device includes a stop element configured to seize the measuring device and to form a sealed casing around the body part of the measuring device, and a housing part arranged to attach to the valve member and to form a sealed casing around the stop element. The placement device is equipped with features that move the stop element seizing the body part of the measuring device inside the housing part so that the measuring device moves between the first position and the second position.

6 Claims, 2 Drawing Sheets

ARRANGEMENT FOR MOVING MEASURING HEAD OF MEASURING DEVICE INTO AND OUT OF PROCESS SPACE

RELATED APPLICATIONS

The present application claims priority under 35 U.S.C. §119 to Finnish Application No. 20055320 filed Jun. 17, 2005, the contents of which are hereby incorporated by reference in their entirety.

BACKGROUND

The invention relates to an arrangement for moving a measuring head of a measuring device into and out of a process space, the arrangement comprising: a valve member to be attached to a wall of the process space; a measuring device to be attached to the valve member, the measuring device comprising a body part provided with an elongated portion which in turn has a measuring head at one end thereof; and a placement device arranged to seize the measuring device and to move it through the valve member into a first position in which the measuring head extends into the process space and, correspondingly, into a second position in which the measuring head is not in contact with the process space.

The above arrangements are currently extremely widely known in different fields of technology. Examples of such fields include food industry, wood processing industry, chemical industry and different research areas. The measuring devices used in these are often optical devices, one advantage of which is that they do not disturb the process. Another advantage is that the measuring operation is stable and adaptable to new process conditions. Moreover, optical measurement is technically reliable. One example of a typical application worth mentioning is the measurement of the properties of black liquor in wood processing industry.

Over the years different arrangements have been proposed in processing industry for moving the measuring head of a measuring device into and out of a process space. A basic idea in these arrangements is to provide equipment that allows the measuring device to be moved out of the process and back into it while the process is running. When such arrangements are used for moving the measuring device, the tip of the device carrying the measuring head passes through a valve member, such as a ball or a slide valve. The measuring device has an elongated arm portion sealed to the valve member mechanics. When the measuring device is outside the valve member, the valve member may be closed, the measuring device being thus safely taken out of the process. The fluid used in the process is often dangerous to the user, i.e. it may be both caustic and hot. In addition, it may be highly pressurized, which further increases the safety risk. One example of such process fluids is the black liquor already mentioned, which is used in pulp industry. The measuring head of the measuring device may be re-inserted into the process by pushing the arm portion through the above-mentioned valve member.

One example that can be mentioned among prior art solutions for moving the measuring head of a measuring device into and out of a process space is the solution described in patent publication FI 84400. This known solution is based on the use of at least two screw bars.

In principle the solution of FI 84400 functions perfectly satisfactorily. A drawback of this solution is, however, that if the sealing between the elongated arm portion of the measuring device and the valve member mechanics is not perfect, process fluid may splatter onto the operator and in the environment during the moving of the measuring device. Another drawback of the solution disclosed in FI 84400 arises from problems relating to the simultaneous rotation of the two screw bars, which render the structure complicated and increase the need for servicing.

It is an object of the invention to provide an arrangement that enables the drawbacks related to the prior art to be eliminated. This is achieved by the arrangement of the invention, characterized in that the placement device comprises a stop element configured to seize the measuring device and to form a sealed casing around the body part of the measuring device, and a housing part arranged to attach to the valve member and to form a sealed casing around the stop element, and in that the placement device is equipped with means for moving the stop element seizing the body part of the measuring device inside the housing part in such a manner that the measuring device moves between the first position and the second position.

An advantage of the arrangement of the invention is above all that any splattering and leakage of process fluid that may take place during the moving of the measuring device do not cause danger to the staff or the environment. This is because the arrangement of the invention forms a completely closed structure around the measuring device so that in case of leakage the process fluid remains inside the arrangement instead of splattering or leaking into the environment. Process fluid that has leaked into the arrangement can be led to a suitable place in a controlled manner, thus eliminating any situations hazardous to the staff and the environment. A further advantage of the invention is that it solves problems related to an implementation involving the use of two screw bars, for example.

BRIEF DESCRIPTION OF THE DRAWINGS

In the following the invention will be illustrated in greater detail with reference to an embodiment used as an example and illustrated in the accompanying drawings, in which.

DETAILED DESCRIPTION

Figure 1:
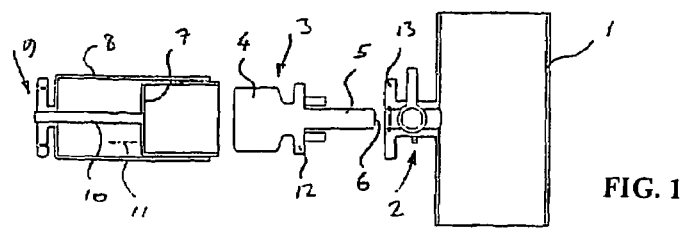
FIG. 1 is a schematic exploded side view of an arrangement of the invention.

FIG. 1 is a schematic exploded side view of an arrangement, measuring device and process space of the invention. The process space is indicated with reference numeral 1. The process space may be a tube, for example, having black liquor flowing therein. FIG. 1 only a shows a part of the tube. Reference numeral 2 indicates a valve member. The valve member 2 may be attached to the process space 1 in any manner known per se, for example by means of a welded stub pipe and a flange joint. The valve member itself may be any type of valve known per se, such as a ball valve, a suitable slide valve, etc. The measuring device is generally indicated with reference numeral 3. The measuring device comprises a body part 4 and an elongated portion 5 arranged thereto and having a measuring head 6 at one end thereof. The body part 4 may contain for example a light source, an analysis circuit, or the like, arranged therein. The measuring head 6 comprises an optical window, for example, which during the measuring comes into contact with the liquid contained in the process space. The measuring device may be any suitable measuring instrument, one example worth mentioning being process refractometer PR-23 of K-Patents.

The arrangement also comprises a placement device arranged to seize the measuring device 3 and to move it through the valve member 2 into a first position in which the measuring head 6 extends into the process space 2 and, correspondingly, into a second position in which the measuring head 6 is not in contact with the process space 2.

Since a person skilled in the art is familiar with the technology related to the above-disclosed valve member and measuring device structures and their operation, these aspects are not discussed in greater detail in this context. Also the operation of the placement device represents prior art known per se to the skilled person on the basis of patent publication FI 84400, for example.

Figure 2:
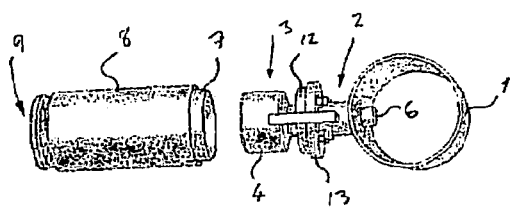
FIG. 2 is a schematic perspective view of the arrangement of the invention in a situation in which the measuring device is attached to the process space for measuring.

According to the invention the placement device comprises a stop element 7 arranged to seize the measuring device 3 and to form a sealed casing around the body part 4 of the measuring device, and a housing part 8 arranged to attach to the valve member 2 and to form a sealed casing around the stop element 7. Further, the placement device is equipped with means 9 for moving the stop element 7 seizing the body part 4 of the measuring device 3 inside the housing part 8 in such a way that the measuring device 3 moves between the first position and the second position. The stop element 7 and the housing part 8 are formed of co-axial casing parts arranged one inside the other, as shown in the Figures. Casing parts formed of cylindrical parts having an annular cross-section have been found particularly advantageous, as shown in FIG. 2 in particular.

The means 9 may be implemented in various ways; the placement device, for example, may comprise a screw bar 10 to be fastened to the stop element 7 and arranged to co-operate with a counter element, i.e. a threaded portion, arranged to the housing part 8. The Figures illustrate this type of embodiment. There are also other ways to implement the placement device. For example, the stop element 7 and the housing part 8 may be implemented so that they form a hydraulic cylinder, the measuring means being then moved according to its operating principle. It is naturally also possible to replace the threaded portion by other suitable means, such as a toothed bar etc.

The outer surface of the stop element 7 and the inner surface of the housing part 8 may be advantageously provided with control members 11 for ensuring the axial movement of the stop element 7 in relation to the housing part 8.

Figure 3:
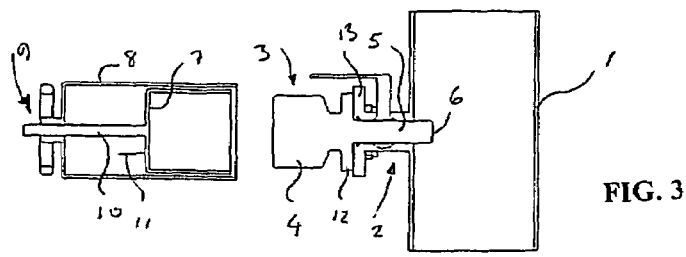
FIG. 3 is a schematic side view of the situation of FIG. 2.

In principle the arrangement of the invention operates as follows. FIG. 3 is a schematic view of the initial situation in which the measuring means 3 is fastened to the process space 1 by means of the valve member 2 so that the measuring head 6 extends into the process space, the measuring head being in contact with process medium contained in the process space or flowing therein.

Figure 4:
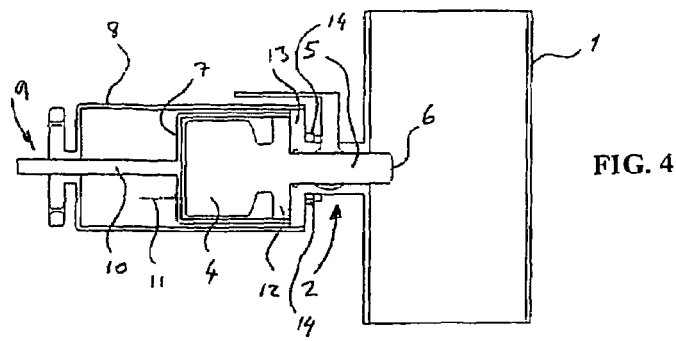
FIG. 4 shows a situation in which the arrangement of the invention is attached to the measuring device.

Every now and then the measuring device 3 must be removed from the process space for servicing, for example. FIG. 4 shows a situation in which the placement device of the invention is fastened to the valve member 2 and to the measuring device 3. The stop element 7 of the placement device is attached to the measuring device 3 by fastening it to a flange portion 12, for example, provided in the measuring device. The housing part 8 in turn is fastened to a flange portion 13 of the valve member 2. The stop element 7 and the housing part 8 may be fastened using any suitable means, such as a bayonet, band, screw, etc. As shown in FIG. 4, the stop element 7 forms a sealed casing around the body part 4 of the measuring device, the housing part 8 in turn forming a sealed casing around the stop element.

Figure 5:
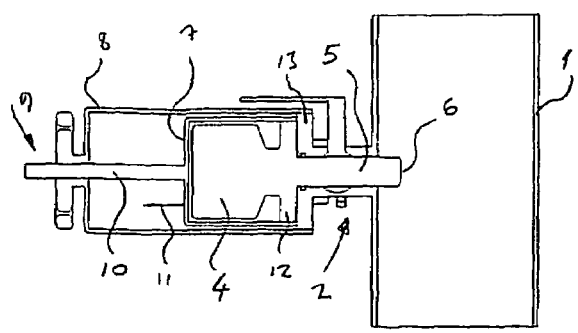
FIG. 5 shows a situation in which the measuring device is detached from the valve member.

FIG. 5 shows a situation in which a bolt-and-screw joint 14 between the measuring device 3 and the valve member 2 is open. FIG. 4 shows the bolt-and-screw joint 14 in its place.

Figure 6:
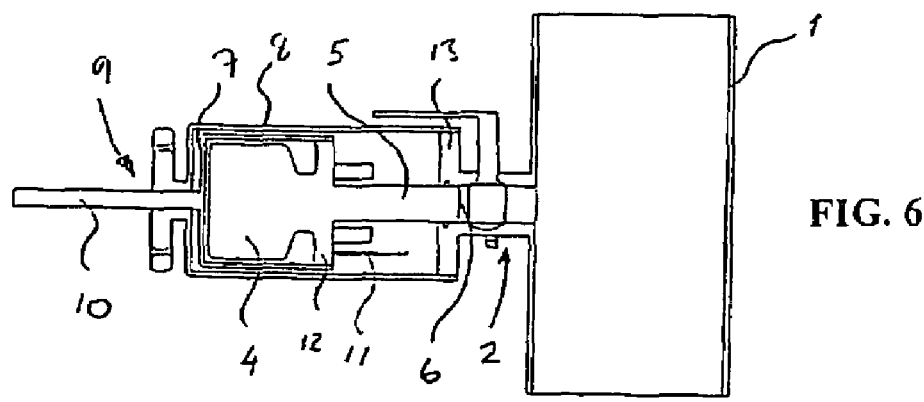
FIG. 6 shows a situation in which the measuring device has been placed into a position in which the measuring head is outside the process space.

FIG. 6 illustrates a situation in which the measuring device 3 has been moved into a position in which the measuring head 6 is out of the process space. In the embodiment of the Figures this is achieved by a screw bar 10. The control members 11 ensure the axial movement of the stop element 7 in relation to the housing part 8.

Figure 7:
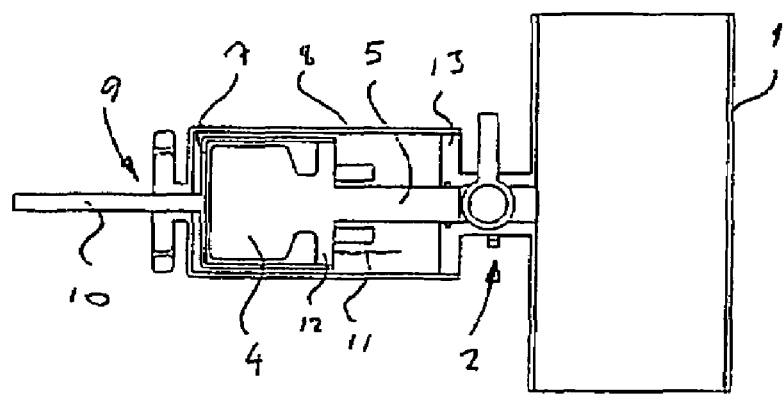
FIG. 7 illustrates a situation in which the valve member has been closed after the measuring device has been moved.

FIG. 7 shows a situation in which the measuring device 3 is in its extracted position and the valve member 2 is closed, whereby the connection between the measuring device 3 and the process space 1 is closed.

Figure 8:
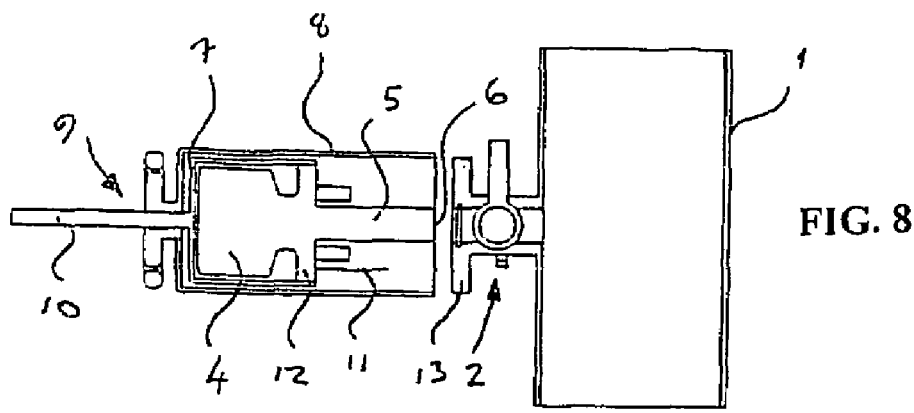
FIG. 8 illustrates a situation in which the arrangement and the measuring device are detached from the valve member.

FIG. 8 shows a situation in which the placement device has been detached from the valve member 2, thus allowing the measuring device 3 to be accessed.

In the next step the measuring device 3 is detached from the placement device. A schematic view of this situation is shown in FIG. 1.

The measuring device is installed back to its place after servicing, for example, by a reverse procedure.

On the basis of the above, it can be concluded that uncontrolled discharge of process medium into the environment through a gap between the valve member 2 and the elongated portion 5 of the measuring device 3 is efficiently prevented, because the process fluid can only leak into the closed space between the stop element 7 and the housing part 8, from where it may be discharged in a controlled manner by means of a suitable fitting, for example.

The embodiment example illustrated in the Figures is in no way meant to restrict the invention, but the invention may be totally freely modified within the scope of the claims. Consequently, it is obvious that the different details of the invention do not necessarily need to be exactly as presented in the Figures, and that other solutions are also possible.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. An arrangement for moving a measuring head of a measuring device into and out of a process space, the arrangement comprising: a valve member to be attached to a wall of the process space; the measuring device to be attached to the valve member, the measuring device comprising a body part provided with an elongated portion which in turn has a measuring head at one end thereof; and a placement device arranged to seize the measuring device and to move it through the valve member into a first position in which the measuring head extends into the process space and, correspondingly, into a second position in which the measuring head is not in contact with the process space, wherein the placement device comprises a stop element configured to seize the measuring device and to form a sealed casing around the body part of the measuring device, and a housing part arranged to attach to the valve member and to form a sealed casing around the stop element, and in that the placement device is equipped with means for moving the stop element seizing the body part of the measuring device inside the housing part in such a manner that the measuring device moves between the first position and the second position.

2. The arrangement according to claim 1, wherein the stop element and the housing part are formed of casing parts arranged co-axially one inside the other.

3. The arrangement according to claim 2, wherein the casing parts are cylindrical.

4. The arrangement according to claim 1, wherein the means for moving the stop element comprise a screw bar to be attached to the stop element and arranged to co-operate with a counter element arranged to the housing part.

5. The arrangement according to claim 1, wherein the outer surface of the stop element and the inner surface of the housing part are provided with control members for ensuring axial movement of the stop element in relation to the housing part.

6. The arrangement according to claim 1, wherein the body part comprises measuring elements such as a light source and analysis circuit.

\* \* \* \* \*